United States Patent [19]

Russ et al.

[11] 4,253,154
[45] Feb. 24, 1981

[54] LINE SCAN AND X-RAY MAP ENHANCEMENT OF SEM X-RAY DATA

[75] Inventors: John C. Russ, Palatine, Ill.; Robert Carey, Asten, Netherlands; Vinod K. Chopra, Vernon Hills, Ill.

[73] Assignee: North American Philips Corporation, New York, N.Y.

[21] Appl. No.: 2,621

[22] Filed: Jan. 11, 1979

[51] Int. Cl.³ .............................................. G06F 15/20
[52] U.S. Cl. ................................. 364/527; 250/311; 358/111; 364/515; 368/118
[58] Field of Search ............... 364/524, 525, 514, 515, 364/527; 358/37, 111; 250/311; 324/78 E, 78 J, 188, 186, 78 D

[56] References Cited

U.S. PATENT DOCUMENTS

| | | | |
|---|---|---|---|
| 3,578,960 | 5/1971 | Georgi et al. | 364/527 |
| 3,812,288 | 5/1974 | Walsh | 358/111 X |
| 3,813,545 | 5/1974 | Barnhart | 358/111 X |
| 3,842,347 | 10/1974 | Terbrack | 324/186 X |
| 3,887,870 | 6/1975 | Grosseau | 324/186 X |
| 3,936,741 | 2/1976 | Coulter et al. | 364/555 X |
| 3,938,038 | 2/1976 | Campbell | 364/555 X |
| 3,968,431 | 7/1976 | Ekstrom | 324/186 X |
| 3,988,602 | 10/1976 | Gorsica, Jr. | 364/515 |
| 4,011,502 | 3/1977 | Fraser | 364/527 X |
| 4,068,310 | 1/1978 | Friauf | 358/166 X |
| 4,156,914 | 5/1979 | Westell | 364/515 |

*Primary Examiner*—Edward J. Wise
*Attorney, Agent, or Firm*—Thomas A. Briody; Robert T. Mayer; Paul R. Miller

[57] ABSTRACT

An improved method and apparatus for obtaining and displaying SEM X-ray line scans and maps for data collection and presentation in energy dispersive X-ray analysis of materials, having ratemeter circuitry providing a voltage output proportional to the intensity of detected pulses in an energy window and an absolute digital representation of the intensity count rate both corrected for dead time, input multiplexing and multiple output buffering of the ratemeter to accomodate multiple channel signals, a feedback loop from said ratemeter to provide display image enhancement, inhibit circuitry to eliminate background signals, signal averging circuitry to permit storage of multiple line scan of multiple single channel analyser outputs in a multi-channel analyser for later processing and display circuitry for displaying stored line scans.

19 Claims, 8 Drawing Figures

LINE SCAN AND X-RAY MAP ENHANCEMENT OF SEM X-RAY DATA

CROSS REFERENCES TO RELATED APPLICATIONS

This application is related to U.S. Patent Applications Ser. No. 897,051, filed Apr. 17, 1978 entitled MULTI-CHANNEL ANALYZER; Ser. No. 897,052, filed Apr. 17, 1978 entitled METHOD FOR DISPLAYING INFORMATION AND APPARATUS THEREFOR; and Ser. No. 964,098, filed Nov. 27, 1978 entitled PROGRAMABLE CONTROL PANEL; all of said applications being owend by the same assignee.

BACKGROUND OF THE INVENTION

1. Field of the Invention

This invention pertains to the field of energy dispersive X-ray fluorescence analysis, and in particular to the processing of data collected by a scanning (and/or transmission) electron microscope (SEM, STEM) and the presentation and storage of the data for meaningful analysis and use both on-line and off-line. Specifically, the apparatus embraces a ratemeter which gives a voltage output proportional to the intensity of the energy window or windows under consideration and additionally an output which is an absolute digital representation of the intensity count rate. The invention includes a new method of dead time correction to enable meaningful single channel intensity data to be handled. The invention further includes input multiplexing and multiple output voltage buffering of the ratemeter to accommodate multiple single channel signals. Furthermore, an extension of the ratemeter is disclosed to enable its use in conjunction with X-ray mapping, thereby permitting enhancements to be made on mapping single channel analyzer data. This enhancement is created by inhibiting single channel analyzer data by using preset values of the intensity count rate of either the channel itself or of other independent single channel analyzer outputs. The invention further includes a new method of storing multiple line scans of multiple single channel analyzer outputs in a multichannel analyzer in a multichannel scaling mode involving signal averaging technique circuits. It further includes a new method of content mapping, a method of processing stored line scans of a scanning electron microscope and means for displaying processed unprocessed stored multiple line scans on the display of a multichannel analyzer and means of displaying processed or unprocessed stored multiple line scans on the display of a scanning electron microscope.

2. Description of the Prior Art

The history of energy dispersive X-ray fluorescent spectrometers is summarized in an article entitled "A Comparison of Wavelength Dispersive and Energy Dispersive X-ray Fluorescent Analysis" by R. Jenkins published in the Edax Editor, Vol. 8, No. 2, April 1978. Among prior art devices to which the invention pertains is the model 711 X-ray energy analyzer manufactured by Edax International Inc., Prairie View, Illinois. This invention specifically will be embodied in the Edax model 9100 series energy dispersive X-ray analysis systems also manufactured by Edax International, Prairie View, Illinois.

Ratemeters

The most common mode of obtaining and presenting an elemental line scan has been to use an analog, or R-C ratemeter, whose input is all of the signal pulses passed by a single channel analyzer. This could be a separate analog module with upper and lower level discriminators, as used in most wavelength-dispersive microprobes, but is more often now a digitally-set energy "window" or "region-of-interest" in the multichannel analyzer memory. The ratemeter uses a resistor-capacitor circuit to continuously time average the rate of pulses. The output voltage, in addition to producing a meter deflection and sometimes as audible signal, can be amplified to drive the vertical deflection axis of the SEM display scope as the beam is slowly scanned along a line across the sample.

This method has the advantage that the information may be readily superimposed (visually or photographically) on the normal SEM picture, so it is easy to judge the correspondence between positions where measured intensity changes occur and features of interest on the specimen. However, there are several common problems with this mode. One lies in the distortion introduced by the R-C circuit, which can cause "tailing" following abrupt changes or mask small changes if the time constant of the R-C circuit is too great, and allow annoying broadening of the line due to statistical fluctuations. The rate and scanning speed for a given measurement can be difficult to achieve.

Somewhat less obvious but in the long run more serious problems in the analog line scan arise from the fact that it is commonly interpreted as a plot of elemental concentration, but is actually a plot of intensity, and measured intensity at that. Changes in sample surface orientation cause such a large change in intensity as to make the line scan meaningless, yet line scans across large irregular particles resting on a substrate are routinely shown to demonstrate the presence of an element. Since the signal which is counted is not just the characteristic X-rays but the continuum falling in the same energy window, it is sometimes possible to record a visually convincing line scan for an element not present at all, if the particle, either because of its surface orientation or density, produces a larger continuum signal than the substrate.

A similar situation occurs when STEM line scans are attempted, since the changes in specimen density (or sometimes thickness) which produce a viewable transmission image usually are reflected in a change in continuum X-ray production. Conventional line scans on thin sections to STEM or irregular surfaces in SEM are in fact meaningless and potentially misleading (as are, also, X-ray maps) but nevertheless often published.

A more subtle yet no less misleading effect on line scan (mis) interpretation is that of varying count rate. Most modern systems incorporate pulse pileup rejection circuits in the amplifier chain, and make a dead time correction by slowing down the system's internal clock when high count rates are encountered. Since the line scan is obtained in real time, as the SEM beam is continuously scanned, the measured signal for the count rate at the energy of interest can be altered greatly by a change in overall system count rate. In some cases this reduces the apparent change in signal; for example if a high concentration of the element being measured occurs in small region of a generally organic sample (or any material emitting few total X-rays) the increase in emitted X-rays as the beam crosses this area also produces an increase in dead time and so fewer of the X-rays are actually processed and passed to the ratemeter.

In the extreme case, high count rates can actually paralyze the system so that the line scan signal is reversed, dropping from a low rate due to the continuum to nearly zero in the high concentration—high count rate region.

In other cases, there may be a change in observed count rate for an element present in an unvarying concentration because of a change in overall count rate, due either to a change in the concentration of another element, or perhaps a change in geometry. Finally, any combination of these effects (count rate, geometry, density, and so forth) may be present to confuse the unwary microscopist.

A typical prior art system configuration for X-ray lines scans consists of an X-ray detecting unit feeding into a preamplifier/amplifier, the output of which goes into a single channel analyzer or alternatively a multichannel analyzer, with digitally set energy windows and associated output circuitry. The pulses coming out of the single channel outputs are representative of incoming detected pulses in the channels of interest and contain not only intensity data due to the element of interest but also of the background intensity level. These pulses are fed into an analog RC-type ratemeter, the output of which is a voltage essentially proportional to the input pulse rate. This voltage is fed to the Y deflection circuitry of the SEM. The single channel pulses can be fed into a pulse shaper and then used to modulate the SEM screen brightness (Z modulation) which creates an X-ray map on the screen when this mode is selected on the SEM.

Multichannel Scaling

Some of the problems inherent in the ratemeter approach are overcome by using a multichannel analyzer (MCA) to store the line scan data. In this mode, the analyzer memory address (channel number) is advanced by an internal time base, and all of the counts in an energy window during one time period are summed in one channel. This eliminates any distortion due to R-C circuit time constants. It also makes possible, at least in theory, the use of multiple sweeps of the SEM beam, to gradually build up data on a sample with short beam exposure when a single slow scan might cause damage. In practice, few systems allow this latter mode of operation, which requires some timing link to sychronize the start of the SEM beam scan with the start of the internal MCA address advance.

The problems of confusion arising from geometry, density and dead-time effects are of course still present in this type of line scan. In addition, it is usually impractical to set a digital energy window to define the X-rays to be counted, since the MCA is being used to store the time-base data, so an analog window is used that is less sharp and more liable to misadjustment. The greatest drawback of the "multichannel scaling" method is that the stored line scan is hard to relate to the SEM image, since the line appears on a different viewing screen and there is no easy correspondence between channel address (time) and image position because the time bases, physical dimensions, and so forth are different. When this mode is used because the SEM has no Y-modulation capability, further distortion may also result since many of the lower-priced SEMS do not have a constant beam sweep speed. If an analog (ratemeter) scan is directly displayed this does not matter, since the same (varying) time base is used for both beam position and display position.

Considering the continued influence of all of the "physical" causes the line scan distortion plus these additional problems, it is indeed unfortunate that the name "digital" line scan has been applied to this mode of operation, implying as it does in current usage a somehow more accurate result.

In this prior art technique known as multichannel scaling, the X-ray detecting unit feeds into a preamplifier/amplifier which feeds into an analog single channel analyzer (SCA) or pulse height selector. Output pulses when created by the SCA are pule shaped in a pulse shaper and scaled in the activated memory channel of the multichannel analyzer. The MCA channel memory address is incremented by a DWELL timer which is iniated by a synchronizing pulse from the X-deflection circuitry of the SEM. The dwell time is dependent on the X-sweep speed of the SEM and the resolution of data required. The contents of the MCA memory at the end of the sweep or multiple sweeps are the line scan data and may be displayed on the display screen of the MCA.

SUMMARY OF THE INVENTION

This invention pertains to a number of improvements for an energy dispersive X-ray analysis system having computer supervised data collection, display and processing. The systems with which the improved circuitry and methods may be used include a dual interlocking bus structure so that the analyzer and computer functions communicate directly with each other and the user has immediate keyboard control of both. Such a system normally includes a system base control, a control console and a display console. The portions of the system which have been improved include a new type of ratemeter which gives a voltage output proportional to the intensity of the energy window or windows under consideration and additionally an output which is an absolute digital representation of the intensity count rate. In both cases, this intensity data is dead time corrected. The improvements further include circuitry for input multiplexing and multiple output voltage buffering of the ratemeter to accomodate multiple single channel signals. The improvements further include a new method of dead time correction to enable meaningful single channel intensity data to be handled by the system. An extension of the ratemeter is also disclosed for use in conjunction with X-ray mapping, enabling enhancements to be made on mapping SCA data. This enhancement is created by inhibiting SCA data by using preset values of the intensity count rate of the SCA data itself or of other independent SCA outputs. The invention further includes a new method of storing multiple line scans of multiple SCA outputs in the multichannel analyzer in the multichannel scaling mode, involving signal averaging techniques and circuits. It further includes a new method of content mapping and a new method of processing stored line scans. It also includes means for displaying processed or unprocessed stored multiple line scans on the display of the multichannel analyzer and means of displaying processed or unprocessed stored multiple line scans on the display of the SEM.

One object of the invention is to make the time base of the data integration exact, to eliminate R-C distortion and to relieve the operator of concern and trouble in setting time constants for every combination of sweep rate and count rate.

To eliminate the R-C analog ratemeter, the invention uses a buffered-output digital integrating ratemeter circuit. In this system it is actually built into the analyzer, for convenience in adjusting the parameters from the main control keyboard. The user-selectable parameters are the integration time (which should usually be set to a time equal to between about one-hundredth and one-fivehundreth of the total line time), the full scale, and a choice of linear or logarithmic scale. The circuit functions by counting all of the incoming pulses (from one of the four independent, simultaneous energy windows set on the analyzer spectrum display, each of which can have multiple segments) for the preset integration time. The resulting number of counts is dead-time corrected to obtain counts-per-(live)-second as described below, divided by the selected full scale value (on either a linear or log scale) and the result expressed as a voltage on the buffered output. This voltage is held at the output for the next integration time period, while a new number of counts is obtained. The process is repeated, so that the complete line scan is actually a series of steps across the sample.

The width of each step depends on the beam sweep speed and the integration time. If the user sets the integration time to less than one-hundredth of the total sweep time, the individual steps are not usually evident in a photographic recording. Integration time settings from 0.001 to 10 seconds are adequate to cover the useful range. The number of counts still is subject to normal statistical considerations, but the line scane is generally free of the "jitter" seen in R-C ratemeter scans using a too-short time constant, while eliminating the tailing problem altogether. Finally, since the output voltage is proportional to counts-per-second it is independent of scan speed (except for statistical effects) and so the operator can change sweep speed at will with no change in ratemeter settings.

The total system configuration consist of an energy dispersive X-ray detecting unit and MCA with a digital dead time corrected ratemeter. The EDS X-ray system is used by way of example only since the ratemeter is also appropriate for any application involving count rates for particle analysis, e.g. nuclear particle counting.

The output of the X-ray detecting unit is amplified and pulse shaped in a preamp/amplifier, each incoming pulse forming a fast discriminator pulse in a fast discriminator which is then counted in a fast discriminator scaler. The pulse output of the amplifier is digitized or pulse rejected in an analog-to-digital converter (ADC) which in turn addresses a multichannel analyzer memory. The address is a function of the energy of the incoming X-ray event. When a pulse arrives in the energy window or windows set by the attribute bits for SCA output, a pulse is sent out to the SCA pulse shaper, the shaped pulses being counted in a pulse scaler. Every time an input pulse is digitized by the ADC and stored by the MCA memory a pulse stored signal is generated by the ADC which feeds into a stored pulse scaler. Under control of timing circuitry, the contents of the fast discriminator scaler and the SCA pulse scaler, fed respectively from the fast discriminator and SCA pulse shaper, together with that of the stored pulse scaler, are loaded into scaler buffer circuitry, and the scalers are reset. Timing is dependent on integration times fed in by the user. The buffered informaton is then used to produce a number equivalent to the dead time corrected intensity level as a count rate. On completion of calculation the corrected intensity is buffered in the intensity buffer, the output of which is a digital representation of SCA intensity and can be used as such, digitally, externally, or can be fed to a digital to analog converter (DAC) whose output after the necessary settling time is an analog representation of intensity count rate in counts per live second, which may be used as a Y modulation signal on a SEM line scan.

A further object of the invention is to provide for input multiplexing and multiple output volage buffering of the improved ratemeter to accommodate multiple single channel signals. This is accomplished by providing multiple inputs to multiple single channel analyzers. These inputs are scaled in multiple scalers which when addressed by the timing circuitry are then loaded into scaler buffers and the scalers then reset. As with the case of single input to the ratemeter, a fast discriminator and a stored pulse scaler are also buffered under the control of the timing circuit. Multiplexer circuitry is provided which can choose one or more of the single channel analyzer inputs on a sequential basis. The sequencing is performed by the timing circuitry. On a sequential basis, as the input from each single channel analyzer is fed to the dead time correction circuitry, its intensity value is calculated and then buffered in an intensity buffer. On the completion of this buffering action, calculation of the next single channel analyzer intensity would begin. The buffered value of the first single channel analyzer intensity is fed out using digital output circuit and also converted into a voltage in a digital-to-analog converter whose output is sampled and held by a sampler hold circuit under the control of the routing switching circuitry. On completion of this cycle, the dead time corrected intensity of the next sample can be buffered in the intensity buffer. The cycle continues sequentially until all outputs have been completed, when the sequence will returned again to the fist input source.

A third object of the invention is to provide a new method of dead time correction to enable meaningful single channel intensity data to be handled. X-ray analysis of samples produces intensity values, which may only be accurately used to compare standard to unknown, or one specimen or location to another, if they are expressed as counts per (live) second. The "dead" time introduced by the detector itself and the processing electronics has been corrected in two ways heretofore, both of which can provide accurate results but suffer from individual practical limitations. (This is in addition to an earlier technique in which the number of counts N per unit clock (or real or elapsed) time is converted to a "dead time corrected" value $N' = N/(1-N_t)$ where t is a presumed constant time associated with the instrument dead time. This method is inexact because t is not a constant, and because the underlying assumption neglects the statistical variation in N, which can be quite large for the low number of counts obtained per point in a line scan. It will not be considered further.

The two accurate methods both make use of a second "fast" analysis channel which amplifis pulses with a short time constant so that events close together in time, which cannot be measured, are rejected (not measured or counted in the stored spectrum). In the Harms method, the total counting time may be fixed (in terms of clock/real/elapsed time). For each pileup event (in which two X-rays are lost) the next successfully processed X-ray is stored as three X-rays instead of one. In other words, the assumption is that the same average distribution of X-rays is rejected as is successfully processed, and the lost counts are made up as they occur. This method is accurate provided that (1) the number of counts processed is great enough that the two counts that may be lost are insignificant, and (2) there are no cases of triple or higher order pileup. However, for finite counting times the method suffers from the limitation that the apparent number of stored counts (including the make-up counts) is larger than the number actually processed but has the actual statistical precision of the (smaller) number actually processed. In other words, it leads to an erroneously good estimate of counting precision unless the percentage dead time is known and used to approximate the actual precision. As the most desirable (high) rates of data collection introduce quite large total amounts of dead time, and multiple pileup does in fact occur, this becomes a serious limitation, and in fact the Harms method is little used.

It has been almost universally supplanted, certainly in commercial instruments, by methods based on keeping track of all of the piled-up (rejected) pulses in a separate counter and periodically stopping the system's internal "live time" clock while that many extra X-rays are successfully processed. This means that the statistical precision of the stored data do obey the normal relationships. The "live time' of the system is always less than the actual elapsed time, however, so that the total clock/real/elapsed time needed to obtain a preset time's worth of data is greater than the elapsed time. The method is accurate provided that the distribution of X-rays arriving later in time is on the average the same as the earlier ones which were rejected. This may be true in the case of (for example) a scanning electron microscope where the beam continuously traverses an inhomogeneous sample. High count rates from high-concentration regions may cause lost pulses from pile-up which may be "made up" subsequently in lower concentration or different areas. Similar problems can arise in on-line monitoring situations, and can only be overcome by keeping the sampling period short enough to resolve the variation. A more significant problem arises, however, in the unpredictable elapsed time which may be needed to acquire one unit of time's worth of data. In many processes (including on-line monitoring and scanning electron microscopy) the period of analysis must be fixed by external events. In that case, the number of X-rays "lost" or "stranded" due to pulse pile-up cannot be mae up and so the measured intensity in counts per (live) second is too low.

The benefits of preset elapsed/real/clock time counting can be combined with accurate dead time correction and pulse pile-up rejection by modifying the method just described in the following novel way. If the live time clock is controlled in the usual way so that during a preset elapsed time T, it measures a live time t, then this value would normally be used to express intensities as the number of counts N for a given peak or element divided by t. This is wrong as described before. However, if the total number of stored counts S and the number of stranded or rejected counts R are used to correct the time t to obtain $t^* = t(1 - R/(S+R))$ then the resulting intensities in counts per live second are exact. This can be done by using either separate counters to keep track of R and S, or by using the total stored spectrum to obtain S, and the same counter used in the normal method to count rejected pulses (to be made up while the clock is stopped) to obtain R. The mathematical calculation can be carried out either by discrete logic, by a stored-program processor in the system, or by pencil and paper if all of the numbers are totalled by the hardware counters and made available to the user. In the case of line scan measurement, the corrected counts-per-(live)-second data are calculated for each integration time period, to form the basis for the output signal.

Another object of the invention is to provide an extension of the ratemeter so that it may be used in conjunction with X-ray mapping, therby enabling enhancements to be made on mapping SCA data. In this invention, the enhancement is created by inhibiting SCA data by using preset values of the intensity count rate of the SCA data itself or other independent SCA outputs. This enables the user to maintain the presentation of the line scan on the SEM display, which can be superimposed on the normal image for best interpretation.

The digital-integrating ratemeter with real time-dead time correction can also be used in conjunction with the "normal" X-ray mapping (dot mapping) mode to produce several novel new displays. First, the user can set a threshold on the ratemeter output (which is displayed on the analyzer TV screen) corresponding to the count rate he associates with background. This threshold can then be used to "gate" the dot output so that in making a map of X-ray dots, any dots occurring in a region where the count rate is below the threshold will not be passed to the SEM display. This functions as a fexible image "enhancer", in which the user can directly adjust the threshold or "background" level in cps and the dimension (the ratemeter integration time) of the enhancement.

However, since the multichannel analyzer can have multiple separate, simultaneously active windows, the enhancement (or threshold-gating as it should more properly be described) can be applied from one element to another. As an example, consider a case in which the ratemeter is monitoring the count rate in an energy window set on an iron peak, and the threshold is adjusted to discriminate between the background intensity and the intensity from the region where iron is present. If a second energy window is set for the sulfer peak, the resulting sulfur dot map will show only those regions containing iron and sulfur. This is quite distinct from the result obtained by setting a conventional window with multiple segments on the iron and sulfur peaks, which would show places where iron or sulfur were present. With the ratemeter output from one element used to discriminate the output of another, and image is obtained which may be interpreted as a map of compounds instead of elements.

Another use to which the digital-integrating ratemeter can be put overcomes the inherent problem of visually integrating an X-ray dot map. Because the human eye/brain combination functions poorly in estimating average dot density, it is usually difficult to see small or gradual intensity changes in a dot map. Only by counting for extremely long times to build up a recorded image with 10 dots or more, each one so faint as to just be discernible on the film, can an image with a recognizeable grey scale be produced in which brightness variations correspond to intensity variations. Since the digital ratemeter can be set to an integration time short enough to allow reasonable sweep speeds, and the real time-dead time correction allows high count rates to be used, it becomes practical to photograph an image that is intensity-modulated by the ratemeter voltage output, so that an X-ray map of brightness rather than discrete dots is obtained. Of course, multiple line scans with deflection-modulation are also possible. Both show two-dimensional patterns of element intensity distribution that would be difficult to see in conventional X-ray dot maps.

An explanation of the enhancement apparatus will be given. By way of example only, this description refers to three independent single channel analyzer outputs of a multichannel analyzer with only one SCA output feeding the ratemeter. However, reference to the multiplexing techniques described above makes it obvious that this limitation is unnecessary. The ratemeter used is the digital dead time corrected ratemeter, but for the purpose of the X-ray map enhancement method, this may be any type of ratemeter, analog, or digital, dead time corrected or not.

The SCA outputs 1, 2 & 3 pass through inhibit gates on their way to the SEM circuitry for Z modulation (or brightness modulation) of the SEM display. The inhibit signals for each channel are independently generated by logic circuitry, said inhibiting signal preventing output of the respective SCA signal to SEM. The V intensity output of the ratemeter is an analog representation of the count rate of the SCA-3 pulse train and this value is compared with a user chosen threshold voltage Y in a voltage comparator, whose output is shaped in pulse shaper to be at the correct logical voltage level for the logic circuitry. Alternatively, a digital comparison may be made in a digital comparator, where the N intensity from the intensity buffer is compared with N threshold, a digital representation of a threshold count rate selected by the user. Again, the output of the comparison is fed to the logic circuitry. In both cases, the output signal of importance from the comparators is the signal indicating that the threshold level is greater than the ratemeter intensity level. The logic circuitry will then inhibit all SCA pulses below the threshold level, in the SCA channels which have been either preprogrammed or selected by the user. Thus, it is possible, for example, to enhance SCA-3 by inhibiting it by its own intensity output, thus removing extraneous background signals from the map; or, for example, to inhibit SCA-1 by the SCA-3 intensity could result in the example of iron and sulphur given above.

Another object of the invention is to provide a new method and circuitry for storing multiple line scans of multiple SCA outputs in the multichannel analyzer in multichannel scaling mode, involving signal averaging techniques. This allows for multiple sweep recording, particularly for SEMS that have no very slow scan ability and for beam sensitive materials.

Further objects of the invention are made possible by the apparatus and methods described heretofore. These further objects include a method of processing stored line scans which allows multiple elements scans to be recorded simultaneously to save time, to aid the user in finding correspondence between patterns of distribution or variation for different elements and to provide the data base to support at least first order correction for geometry intensity effects and second element effects. This further enables the system to provide a new method of content mapping, a means for displaying processed or unprocessed stored multiple line scans on the display of the multichannel analyzer and means of displaying processed or unprocessed stored multiple line scans on the display of the SEM.

Rather than use the words "analog" and "digital" to describe line scans, as has been previous usage, we prefer the term "real-time" to describe the mode of operation of the buffered-output integrating ratemeter just described. This in a sense replaces the older "analog" or R-C ratemeter, though of course it uses digital logic to do so. The other type of line scan described previously the so-called "digital" or MCS (multichannel scaling) line scan, is superseded in this invention by a new type of stored line scan. In this mode of operation, the same ratemeter circuit and same digital energy window(s) function to produce a dead-time corrected value of counts-per-(live)-second, but instead of being passed to the SEM display vertical deflection amplifier as a voltage, it is stored in the MCA memory. Note that unlike the older method, which stored counts, this method stores corrected counts-per-second. Also, since there are multiple simultaneously but separately active energy windows in the MCA, we can simultaneously store multiple line scans for different elements or energy windows (each one with multiple segments if desired).

By way of example only this description will further refer to an MCA with four SCA outputs.

The resulting display on the multichannel analyzer video screen is particularly effective with color-coding, assigning a different color to the dots of each element's line which shows clearly the correspondence between patterns of element distributions.

Since the data are stored, it requires only a triggering pulse either from analyzer to SEM (to start the beam sweep) or conversely (to start the memory address advance) to make it possible to build up a set of line scans by repetitive scanning. Since the vertical scale of the display is counts-per-second, the data are signal-averaged so that with each successive sweep the new value is averaged with the old ones, with appropriate weighting based on the number of sweeps. For the nth sweep, if the previously stored count rate value was $R_0$ and the new value is $R_1$ then the subsequently stored value will be $$\frac{(n-1)}{n} R_0 + \frac{1}{n} R_1$$

In this way the statistical quality of the stored and displayed line scans improves, but the vertical scale does not change. Since the analyzer memory has a total of 4000 channels, and scans for four elements can be simultaneously stored, it is possible to select a time base for the integration that uses up to 1000 points for the length of the beam scan across the sample. The cursor indicates the position along the horizontal scale if the user has entered the correpondence between time and position, and if that relationship is linear. All four scans are displayed superimposed and color coded.

The operation of the stored line scan circuitry uses the ratemeter, the intensity buffer and the DAC. Gating circuitry and the control logic circuitry have been added. The control logic can be hardware, software or firmware programmed microprocessor circuitry and can be integrated with the timing circuitry and dead time correction circuit.

When storing line scan data the gating circuitry routes N intensity to the MCA memory, or to any other memory configuration or device. The line scans in the four SCA example, would involve sequential storing of SCA 1, 2, 3 & 4 intensity data and repeating this cycle until the scan is completed or memory is full. The timing of memory address is achieved using MCS timing logic which can either be synchronized from the SEM display or can trigger the SEM display. When storing and simultaneously displaying data, a first gate routes intensity data to the MCA and to another gate which routes the desired SCA output to the DAC and hence to the SEM screen. When replaying stored data on the SEM screen, the second gate routes intensity data from the MCA memory to the DAC and hence to the display. The MCS timing circuitry together with the calculation circuitry of the MCA achieves the signal averaging described above.

If the beam sweep is not confined to a single line, but is allowed to raster over the entire image area, the multiple-sweep storage mode can be used to produce a content map. In this case, the user selects a number of "image points" for the entire picture area, which can practically range from 100×100 down to as little as 25×25. All of the information in the square area centered around each point of the image can then be automatically averaged and ultimately can be displayed as a content map. An example would be a beam scanning 1000 lines on a sample, and for each line the horizontal sweep is subdivided by the integrating time of the ratemeter and channel address in the MCA into 1000 points. If the first twenty sweeps are signal averaged as described above under stored line scans, and then the contents (which are in counts-per-(live)-second) of each group of twenty channels in the scan for each element are averaged, it results in 50 numbers. These are transferred into computer storage, and the process repeated for the next twenty beam scans, and so on.

The result is an array of 50×50 corrected intensity values for each of four elemental energy windows. These data can be "played back" to the SEM display as a brightness-modulated "checkerboard" image for one element at a time, using the ratemeter output circuit as described before. Not only can various selections of full scale and log/linear display be used on the stored data, but in addition the content-map image is quite readily interpretable to the eye, in spite of its comparatively poor resolution and small number of image points.

When multiple element line scans are simultaneously stored, it becomes interesting to use simple modes of data processing to combine them. In many cases the user is interested not so much in the variation of one element across the sample as in the relationship between variations of several elements. This is difficult to study with conventional line scans taken one at a time, and even hard to see in the simultaneous scans presented together. By adding the capability to store the multiple scans and display any arithmetic combination of them, one introduces the possibility to see the relationships more clearly.

For example, it may be clear that both Ca and Si increase or decrease in the same grains of a material, but by displaying the ratio of Ca/Si (or the inverse) one can see whether the stoichiometry remains essentially the same (neglecting second order effects which would require a full ZAF computation) or not.

A particularly useful extension of this combination or ratioing method results when one of the four energy windows is set on background (typically with several window segments on different portions of the continuum). The background intensity can be used to overcome, to a first order approximation, many of the geometry and density problems described previously.

For example, in a thin section in STEM, the ratio Ca/BG will show real variations in calcium localization independent of the density change associated with the precipitates. Since subtraction can also be easily computed point-by-point on the line scans, it is even better to display the net calcium variation (Ca-BG)/BG for this case.

For bulk samples, the effects of surface geometry can be partially compensated by setting a background window at an energy near the peak of an element of interest, for example Fe in a sample also containing S. The effect of changing surface orientation, which particularly changes the absorption path length of the X-rays, is similar for the characteristic X-rays and for the continuum X-rays of nearly the same energy. Hence the problem can be largely compensated, using the (Fe-BG)/BG signal. The ratio of Fe to S in this specimen is also shown to be uniform by the plot of $$\frac{(Fe - BG)/BG}{(S - BG)/BG}$$

where in this case two background windows were set up at energies near the Fe and S peaks. The system allows any arithmetic combination of terms to be selected.

Finally, the same advantages of combining line scans from several elements can also be realized with the stored array of intensities described under content mapping, so that element/element, element/background, and other combinations can be displayed.

Manipulation of stored data involves addressing the stored SCA intensities in the MCA memory and calculating the necessary combinations in external computer hardware. When completed, the processed data can be fed back into the MCA.

By storing the SCA data in alternate memory channels of the MCA it is possible using the normal display means of the MCA to display the stored data.

Although the mode just described can often be viewed and interpreted directly, especially in cases where changes in intensity for one element correspond (positively or inversely) to changes in another, it is still clearly desirable to be able to view and/or photograph the line scan on the SEM display, where it will be in proper registration with the image.

This can readily be accomplished using the existing buffer output circuitry of the ratemeter, normally used for real-time scans. If as the beam scans across the sample, the counts-per-(live)-second data are taken from one of the stored line scans in memory and used to generate the output voltage that is passed to the vertical deflection axis of the SEM display, it appears there the same as a real-time scan. This means that multiple-sweep data can be accumulated and the "played out" for viewing, or the data can be taken once and then re-played on the display with different full-scale (or linear/logarithmic) selections.

To summarize the points of novelty in the present invention, the system disclosed herein produces line scans with no time constant R-C effects; it uses exact digital energy windows set on the spectrum display; it corrects data for count rate and dead time effects; it presents the line scans on the scanning electron microscope in registration with image; it allows for multiple sweeps to build up in the line scans; it corrects for geometry, density, and second element effects; and it collects multiple line scans simultaneously. In addition, the equipment needed to achieve these various novel points can also be used to extend some of the same features to area scans in the form of enhanced dot maps, content maps, and compound maps. Line scans and area scans contain much information about element distribution and hence are attractive to the scanning electron microscopist. By making the information obtained more accurate and interpretable, this invention provides a valuable tool in conjunction with the STEM and STM.

DESCIPTION OF THE PREFERRED EMBODIMENT

This invention pertains to improvements in any energy dispersive X-ray analysis system under computer control. The system for which these improvements are particularly useful embodies a system base console, a control console and a display console for use with energy dispersive X-ray data gathering and data processing. The system furthermore incorporates a dual interlocking bus structure so that the X-ray analyzer and the computer functions communicate directly with each other, putting the user in immediate keyboard control of both. A fast four thousand channel analyzer accumulates and displays X-ray spectra under interactive control and supervision by a built-in computer via a bus translator. Since the computer in the system does not need to sort, store and display the spectrum, it is free to process previously accumulated data simultaneously in real time while it supervises a 4000 channel anaylzer according to the user's instructions entered over a common keyboard control. The improvements in such a system which are disclosed herein will be described with reference to the drawings.

Figure 1:
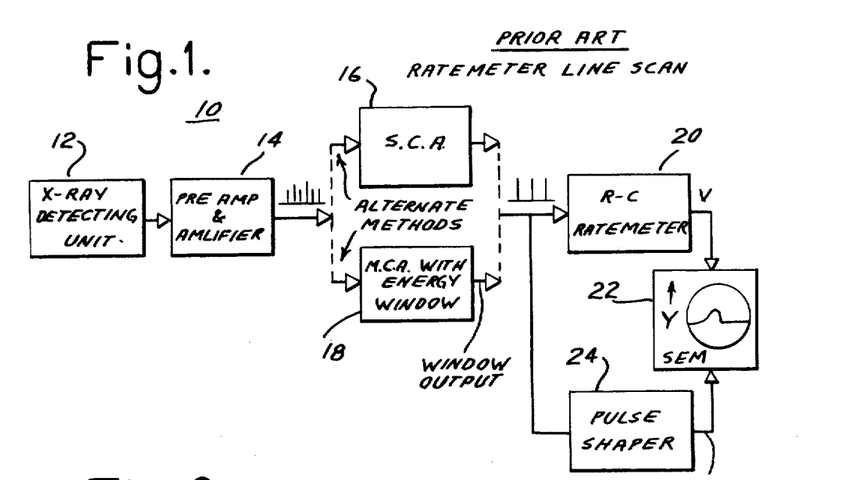
FIG. 1 is a block diagram of a prior art ratemeter configuration for X-ray line scans.

FIG. 1 shows a typical prior art configuration for X-ray line scans. System 10 consists of an X-ray detecting unit 12 feeding into a preamplifier/amplifier 14, the output of which goes into a single channel analyzer 16, or alternatively a multichannel analyzer 18, with digitally set energy windows and associated output circuitry. The pulses coming out of the single channel outputs are representative of incoming detected pulse in the channels of interest and contain not only intensity data due to the element of interset but also of the background intensity level. These pulses are fed into an analog RC-type ratemeter 20, the output of which is a voltage essentially proportional to the input pulse rate. This voltage is fed to the Y deflection circuitry of the SEM 22. In FIG. 1 the single channel pulses can be fed into a pulse shaper 24 and then used to modulate the SEM screen brightness (Z mod) which creates an X-ray map on the screen when this mode is selected on the SEM.

Figure 2:
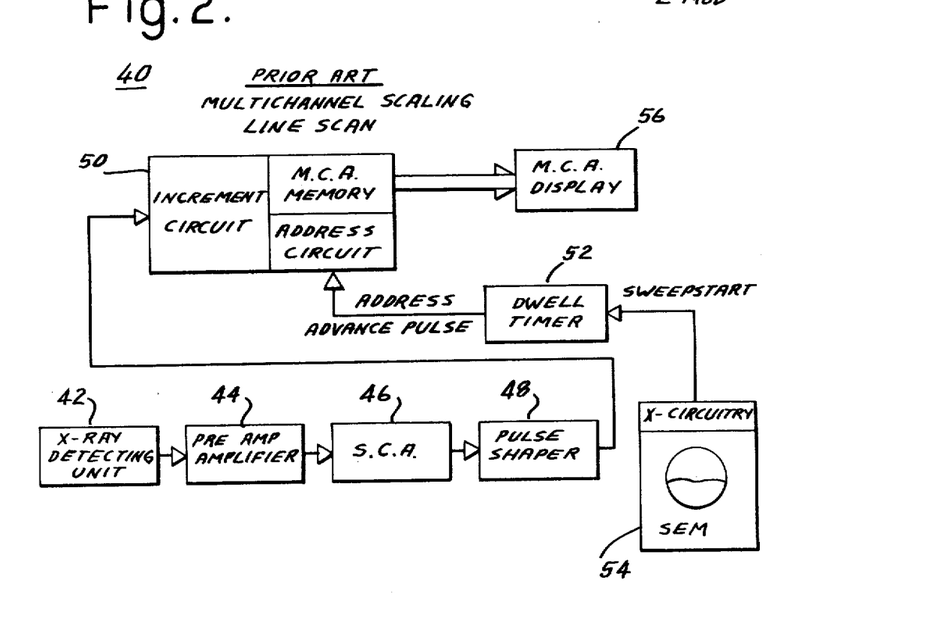
FIG. 2 is a block diagram of a prior art multichannel scaling system for X-ray line scans.

FIG. 2 illustrates a prior art system 40 known as multichannel scaling. The X-ray detecting unit 42 feeds into a preamplifier/amplifier 44 which feeds into an analog single channel analyzer or pulse height selector 46. Output pulses when created by the SCA are pulse shaped in pulse shaper 48 and scaled in the activated memory channel of the multichannel analyzer 50. The MCA channel memory address is incremented by a DWELL timer 52 which is initiated by a synchronizing pulse from the X deflection circuitry of the SEM 54. The dwell time is dependent on the X -sweep speed of the SEM and the resolution of data required. The contents of the MCA memory at the end of the sweep or multiple sweeps are the line scan data and may be displayed on the display screen 56 of the MCA 50.

DIGITAL DEAD TIME CORRECTED RATEMETER

To eliminate the R-C analog ratemeter, the present invention used a buffered-output digital integrating ratemeter circuit. In this example it is acutally built into the analyzer, for convenience in adjusting the parameters from the main control keyboard. The user-selectable parameters are the integration time (which should usually be set to a time equal to between about one-hundredth and one-fivehundreth of the total line time), the full scale, and a choice of linear or logarithmic scale. The circuit functions by counting all of the incoming pulses (from one of the four independent, simultaneous energy windows set on the analyzer spectrum display, each of which can have multiple segments) for the preset integration time. The resulting number of counts is dead-time corrected to obtain counts-per-(live)-second as described below, divided by the selected full scale value (on either a linear or log scale) and the result expressed as a voltage on the buffered output. This voltage is held at the output for the next integration time period, while a new number of counts is obtained. The process is repeated, so that the complete line scan is actually a series of steps across the sample.

The width of each step depends on the beam sweep speed and the integration time. If the user sets the integration time to less then one-onehundredth of the total sweep time, the individual steps are not usually evident in a photographic recording. Integration time settings from 0.01 to 10 seconds are adequate to cover the useful range. The number of counts still is subject to normal statistical considerations, of course, but the line scan is generally free of the "jitter" seen in R-C ratemeter scans using a too-short time constant, while eliminating the tailing problem altogether. Finally, since the output voltage is proportional to counts-per-second it is independent of scan speed (except for statistical effects) and so the operator can change sweep speed at will with no change in ratemeter settings.

Figure 3:
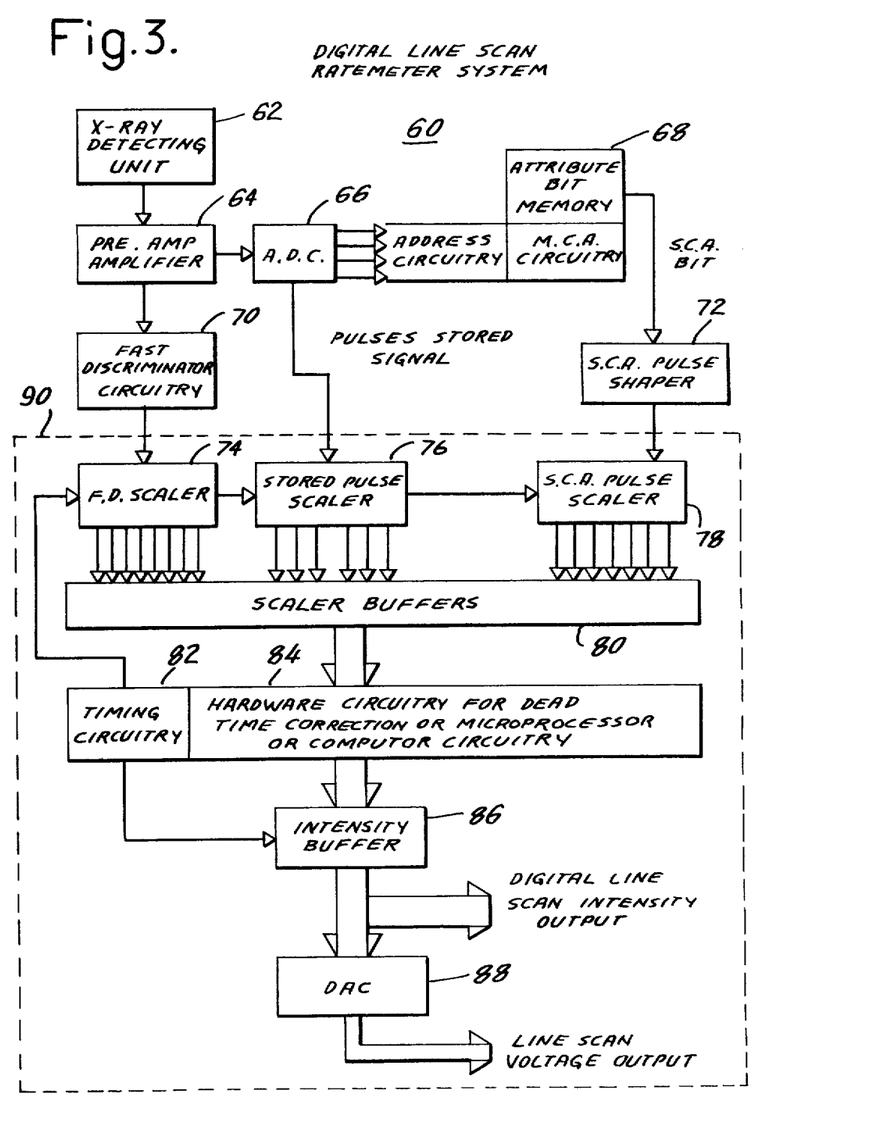
FIG. 3 is a block diagram of a digital line scan ratemeter system according to the present invention.

Referring to FIG. 3, the operation of the ratemeter will be explained. The total system configuration 60 consists of an energy dispersive X-ray detecting unit 62 and multichannel analyzer (MCA) 68 with a digital dead time corrected ratemeter 90. The energy dispersive X-ray system is used by way of example only since the ratemeter is also appropriate for any application involving counts rates for particle analysis, e.g. nuclear particle counting.

The output of the X-ray detecting unit 62 is amplified and pulse shaped in the preamp/amplifier 64, each incoming pulse forming a fast discriminator pulse in the fast discriminator 70. These pulses are counted in fast discriminator scaler 74. The pulse output of the amplifier 64 is digitized or pulse rejected in the analog-to-digital converter (ADC) 66 which in turn addresses a multichannel analyzer memory 68. The address is a function of the energy of the incoming X-ray event. The memory shown as 68 in FIG. 3 incorporates the attribute bit memory described in U.S. patent application, Ser. No. 897,052, filed Apr. 17, 1978. When a pulse arrives in the energy window or windows set by the attribute bits for single channel analyzer (SCA) output a pulse is sent out to the SCA pulse shaper 72. These pulses are counted in SCA pulse scaler 78. Every time an input pulse is digitized by the ADC 66 and stored by the MCA memory 68 a pulse stored signal is generated by the ADC which feeds into a stored pulse scaler 76. Under control of timing circuitry, 82, which may be hardware or software, or firmware, programmed microprocessor circuitry, the contents of the fast discriminator scaler 74 and the SCA pulse scaler 78, fed respectively from the fast discriminator 70 and SC pulse shaper 72, together with that of the stored pulse scaler 76, are loaded into the scaler buffer circuitry 80, and the scalers 74, 76 and 78 reset. Timing of 82 is dependent on integration times fed in by the user as previously described. The buffered information is then used to produce a number equivalent to the dead time corrected intensity level as a count rate in 84 which is either special purpose hard wired logic or a preprogrammed microprocessor. The calculation method is described hereafter. On completion of calculation, the corrected intensity is buffered in the intensity buffer 86, the output of which is a digital representation of SCA intensity and can be used as such, digitally, externally, or can be fed to a digital-to-analog converter (DAC) 88 whose output after the necessary settling time is an analog representation of intensity count rate in counts-per-live-second, which may be used as a Y modulation signal on an SEM line scan.

As used herein, a scaler is a digital counter, the terminology deriving from the terminology used in nuclear partical counting.

DIGITAL DEAD TIME CORRECTED RATEMETER WITH MULTIPLE INPUTS

Figure 4:
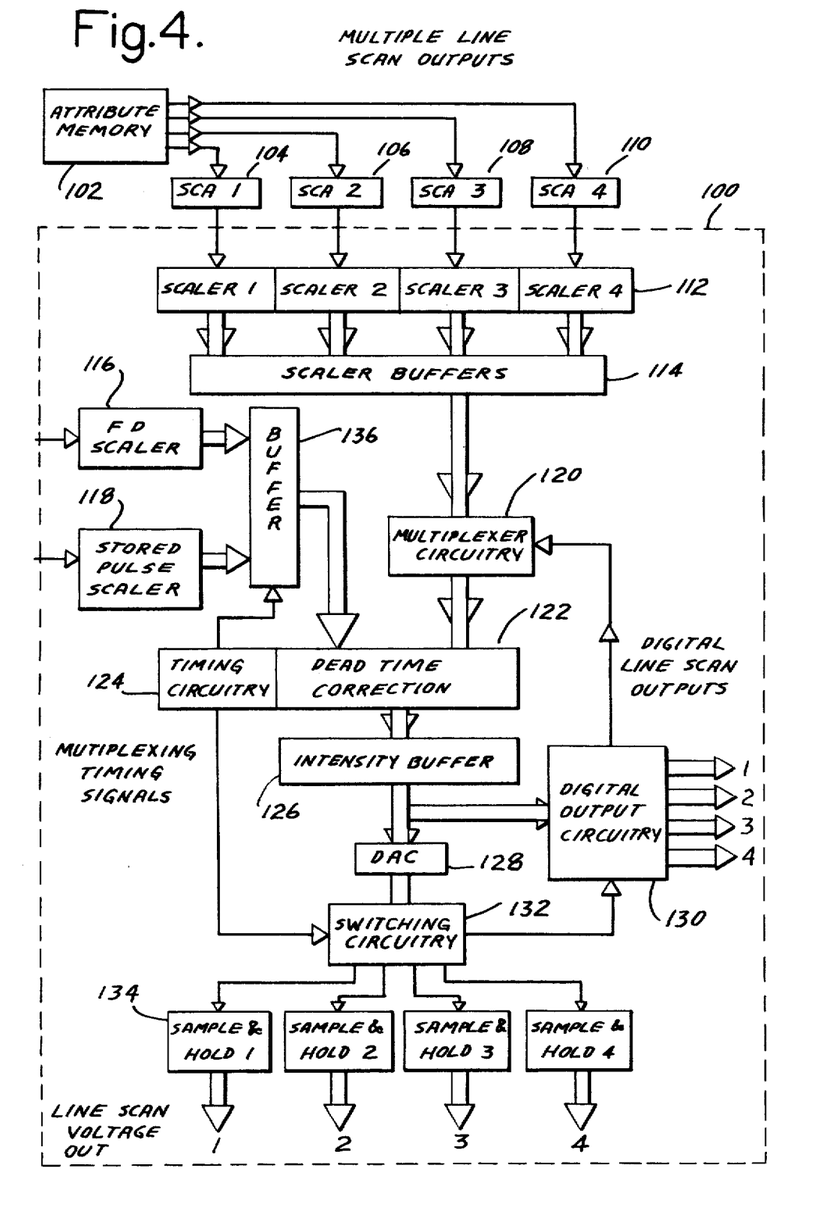
FIG. 4 is a block diagram of the ratemeter of FIG. 3 with multiple line scan input and outputs.

Referring to FIG. 4, the apparatus 100 embodies the dead time corrected ratemeter 90 of FIG. 3 with multiple inputs. The attribute memory 102 and the SCA circuits 104, 106, 108 and 110 are the items 68 and four times 72 of FIG. 3. Thus, the outputs of circuits 104, 106, 108 and 110 represent multiple single channel outputs which, by way of illustration and example only, are four outputs. As in the previous case, the SCA input is scaled, this time in four scalers 112, which when addressed by the timing circuitry 124 are loaded into scaler buffers 114 and the scalers 112 reset. Again, the fast discriminator scaler 116 and stored pulse scaler 118 are buffered in buffers 136, also under control of the timing circuit 124. The multiplexer circuitry 120 can choose one of the SCA inputs; or more, on a sequential basis. The sequencing again is performed by the timing circuit 124. Thus, on a sequential basis of 1 thru 4, the action would be as follows: SCA-1 scaler would be fed to the dead time correction circuitry 122 where the intensity value would be calculated and buffered in the intensity buffer 126. On completion of this buffering action, calculation of SCA-2 intensity would begin. The buffered value of SCA-1 intensity would be fed out using the digital output circuit 130 on line 1 and also converted into a voltage in the DAC 128 whose output would be sampled and held by the sample and hold circuit 1, 134, which is an analog buffer, under control of the routing switching circuit 132. On completion of this cycle, the dead time corrected intensity of sample 2 can be buffered in intensity buffer 126 and the cycle continues sequentially until all outputs have been completed, when the sequence will return to SCA 1.

A NEW METHOD OF DEAD TIME CORRECTION

X-ray analysis of samples produces intensity values, which may only be accurately used to compare a standard to an unknown, or one specimen or location to another, if they are expressed as counts per (live) second. The "dead" time introduced by the detector itself and the processing electronics has been corrected in two ways heretofore, both of which can provide accurate results but suffer from individual practical limitations as discussed above.

The benefits of the present elapsed/real/clock time counting can be combined with accurate dead time correction and pulse pile-up rejection by modifying the method described previously in the following novel way. If the live time clock is controlled in the usual way so that during a preset elapsed time T, it measures a live time t, then this value would normally be used to express intensities as the number of counts N for a given peak or element divided by t. This is wrong as described before. However, if the total number of stored counts S and the number of stranded or rejected counts R are used to correct the time t to obtain $t^* = t(1-(R/(S+R))$, then the resulting intensities in counts per live second are exact. This can be done by using either separate counters to keep track of R and S, or by using the total stored spectrum to obtain S, and the same counter is used in the normal method to count rejected pulses (to be made up while the clock is stopped) to obtain R. The mathematical calculation can be carried out either by discrete logic, by a stored-program processor in the system, or by pencil and paper if all of the numbers are totalled by the hardware counters and made available to the user. In the case of line scan measurement, the corrected counts-per-(live)-second data are calculated for each integration time period, to form the basis for the output signal. This is computed in circuit 84 of FIG. 3 or circuit 122 of FIG. 4.

METHOD OF X-RAY MAP ENHANCEMENT AND CONTENT MAPPING

The digital-integrating ratemeter 90 (FIG. 3) or 100 (FIG. 4) with real time-dead time correction can also be used in conjunction with the "normal" X-ray mapping (dot mapping) mode to produce several novel new displays. First, the user can set a threshold on the ratemeter output (which is displayed on the analyzer TV screen) corresponding to the count rate he associates with background. This threshold can then be used to "gate" the dot output so that in making a map of X-ray dots, any dots occurring in a region where the count rate is below the threshold will not be passed to the SEM display. This functions as a flexible image "enhancer", in which the user can directly adjust the threshold or "background" level in cps and the dimension (the ratemeter integration time) of the enhancement.

However, since the multichannel analyzer can have multiple separate, simultaneously active windows, the enhancement (or threshold-gating as it should more properly be described) can be applied from one element to another. As an example, consider a case in which the ratemeter is monitoring the count rate in an energy window set on an iron peak, and the threshold is adjusted to discriminate between the background intensity and the intensity from the region where iron is present. If a second energy window is set for the sulfur peak, the resulting sulfur dot map will show only those regions containing iron and sulfur. This is quite distinct from the result obtained by setting a conventional window with multiple segments on the iron and sulfur peaks, which would show places where iron or sulfur were present. With the ratemeter output from one element used to discriminate the output of another, an image is obtained which may be interpreted as a mpa of compounds instead of elements.

Another use to which the digital-integrating ratemeter can be put overcomes the inherent problem of visually integrating an X-ray dot map. Because the human eye/brain combination functions poorly in estimating average dot density, it is usually difficult to see small or gradual intensity changes in a dot map. Only by counting for extremely long times to build up a recorded image with 10 dots or more, each one so faint as to just be discernible on the film, can an image with a recognizable grey scale be produced in which brightness variations correspond to intensity variations. Since the digital ratemeter can be set to an integration time short enough to allow reasonable sweep speeds, and the real time-dead time correction allows high count rates to be used, it becomes practical to photograph an image that is intensity-modulated by the ratemeter voltage output, so that an X-ray map of brightness rather than discrete dots is obtained. Of course, multiple line scans with deflection-modulation are also possible. Both show two-dimensional patterns of element intensity distribution that would be difficult to see in conventional X-ray dot maps.

Figure 5:
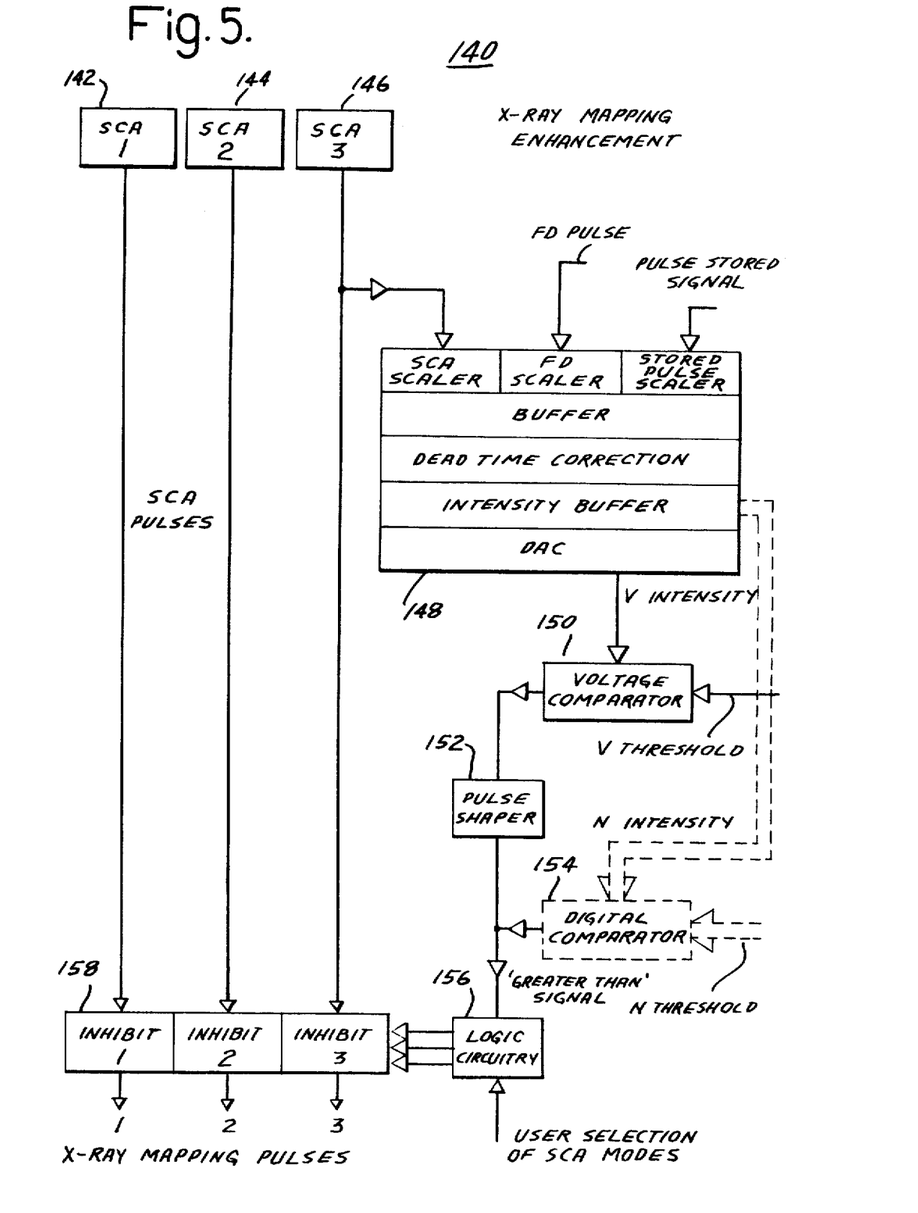
FIG. 5 is a block diagram of the X-ray mapping enhancement provided for the system of the present invention.

Referring to FIG. 5, an explanation of the enhancement apparatus will be given. By way of example only, this description refers to three independent single channel analyzer outputs of a multichannel analyzer 142, 144, 146 with only SCA-3 output feeding the ratemeter 148. However, reference to the multiplexing techniques of FIG. 4 makes it obvious that this limitation is unnecessary. The ratemeter 148 is shown as the digital dead time corrected ratemeter of FIG. 3, but for the purpose of the X-ray map enhancement method, this may be any type of ratemeter, analog, or digital, dead time corrected or not.

The SCA outputs 1, 2 & 3 (142, 144 & 146) pass through inhibit gates 158 on their way to the SEM circuitry for Z modulation (or brightness modulation) of the SEM display. The inhibit signals for each channel are independently generated by logic circuitry 156, which is elementary combinatorial logic, said inhibiting signal preventing output of the respective SCA signal to SEM. In the example, the V intensity output of the ratemeter is an analog representation of the count rate of the SCA-3 pulse train and this value is compared with a user chosen threshold voltage, V threshold, in a voltage comparator 150, whose output is shaped in pulse shaper 152 to be at the correct logical voltage level for the logic circuitry 156. Alternatively a digital comparison may be made in the digital comparator 154, where the N intensity from 148 is compared with N threshold, a digital representation of a threshold count rate selected by the user. Again, the output of the comparison is fed to the logic circuitry 156. In both cases, the output signal of importance from the comparators 150 and 154 is the signal indicating that the threshold level is greater than the ratemeter intensity level. The logic circuitry 156 will then inhibit all SCA pulses below the threshold level, in the SCA channels which have been either preprogrammed or selected by the user. Thus, it is possible, for example, to enhance SCA-3 by inhibiting it by its own intensity output, thus removing extraneous background signals from the map; or, for example, to inhibit SCA-1 by the SCA-3 intensity could result in the example of iron and sulphur given above.

STORED LINE SCANS

Rather than use the words "analog" and "digital" to describe line scans, as has been previous usage, we prefer the name real-time to describe the mode of operation of the buffered-output integrating ratemeter just described. This in a sense replaces the older "analog" or R-C ratemeter, though of course it uses digital logic to do so. The other type of line scan referred to in the introduction, the so-called "digital" or MCS (multichannel scaling) line scan, we have superseded by a new type of stored line scan. In this mode of operation the same ratemeter circuit and same digital energy window(s) function to produce a dead-time corrected value of counts-per-live-second, but instead of being passed to the SEM display vertical deflection amplifier as a voltage, it is stored in the MCA memory. Unlike the older method, which stored counts, this method stores corrected counts-per-second. Also, since there are multiple simultaneously but separately active energy windows in the MCA, we can simultaneously store multiple line scans for different elements or energy windows (each one with multiple segments if desired).

By way of example only this description will further refer to an MCA with four SCA outputs.

Figure 7:
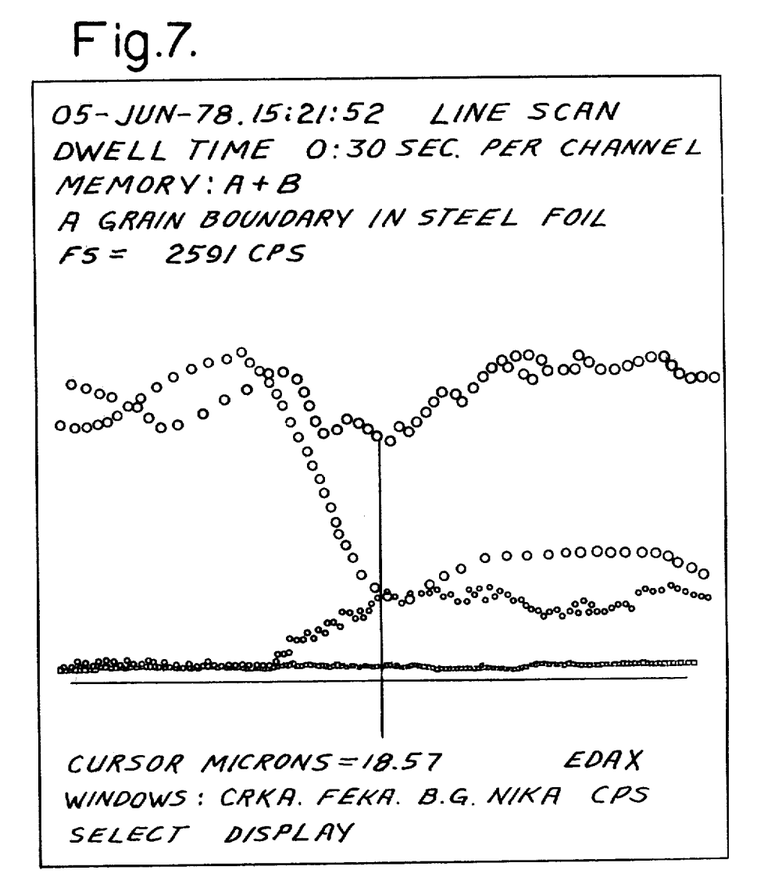
FIG. 7 is a simulated presentation of a typical display showing the presentation of simultaneous line scans which have been priviously stored.

The resulting display on the multichannel analyzer video screen is particularly effective with color-coding, assigning a different color to the dots of each element's line. FIG. 7, being reproduced in black and white, loses some of the impact of the color but still shows clearly the correspondence between patterns of element distribution.

Since the data are stored, it requires only a triggering pulse either from the analyzer to the SEM (to start the beam sweep) or conversely (to start the memory address advance) to make it possible to build up a set of line scans by repetitive scanning. Since the vertical scale of the display is counts-per-second, the data are signal-averaged so that with each successive sweep the new value is averaged with the old ones, with appropriate weighting based on the numbers of sweeps. For the nth sweep, if the previously stored count rate value was $R_0$ and the new value is $R_1$ then the subsequently stored value will be $$\frac{(n-1)}{n} R_0 + \frac{1}{n} R_1$$

In this way the statistical quality of the stored and displayed line scans improves, but the vertical scale does not change. Since the analyzer memory has a total of 4000 channels, and scans for four elements can be simultaneously stored, it is possible to select a time base for the integration that uses up to 1000 points for the length of the beam scan across the sample. The cursor indicates the position along the horizontal scale if the user has entered the correspondence between time and position, and if that relationship is linear. All four scans are displayed superimposed and color coded.

Figure 6:
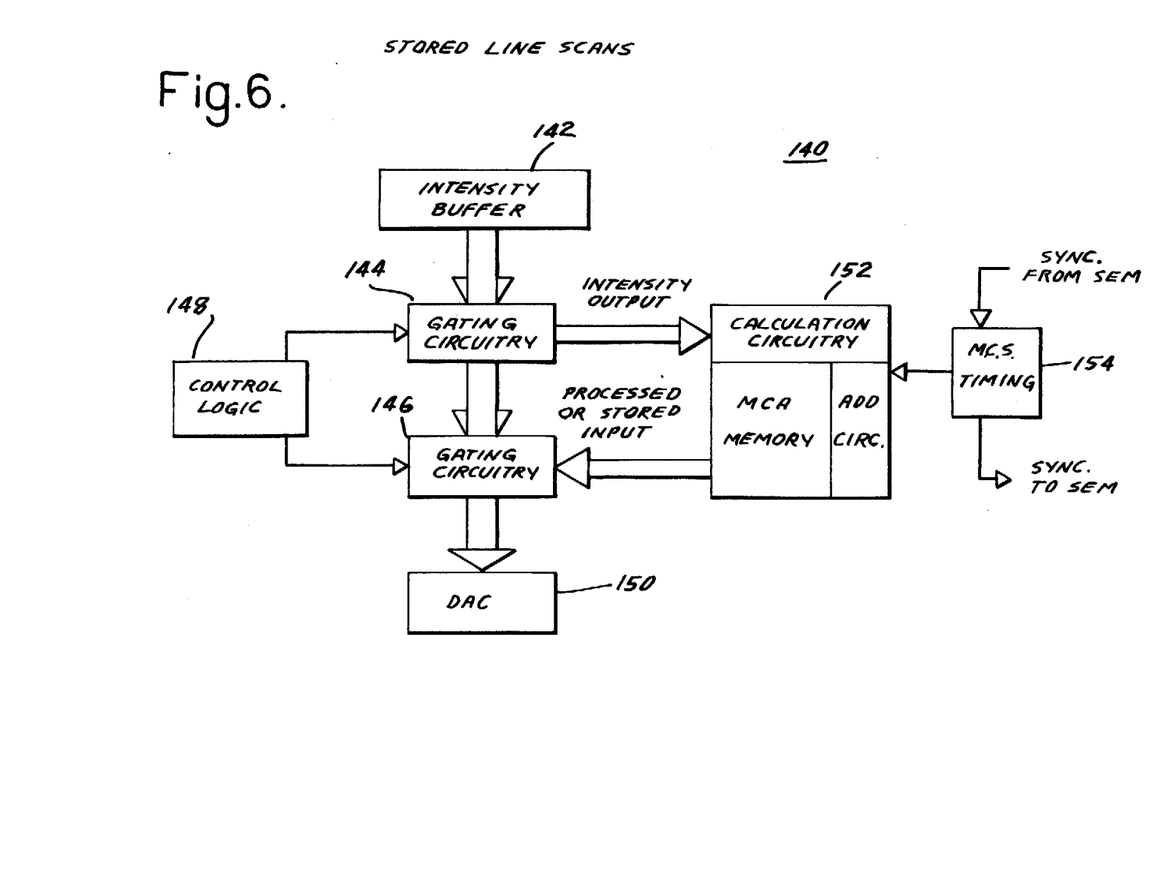
FIG. 6 is a block diagram of the system for providing stored line scans according to the invention.

The operation of the stored line scan circuitry is explained by reference to FIG. 6, using the ratemeter 100 of FIG. 4. The intensity buffer 142 and DAC 150 are equivalent to 126 and 128 respectively of FIG. 4, gating circuitry 144 and 146 under the control of logic circuitry 148 have been added. The control logic 148 can be hardware, software or firmware programmed microprocessor circuitry and can be implemented into the timing circuitry 124 and dead time correction 122 of FIG. 4. Control logic 148 is elementary combinatorial logic.

When storing line scan data, the gating circuitry 144 routes N intensity to the MCA memory 152, or to any other memory configuration or device. The line scans, in the four SCA example, would involve sequential storing of SCA-1, 2, 3 & 4 intensity data and repeating this cycle until the scan is completed or memory is full, timing of memory address is achieved using MCS timing logic 154 which can either be synchronized from the SEM display or can trigger the SEM display. When storing and simultaneously displaying, first gate 144 routes intensity data to the MCA 152 and to second gate 146 which routes the desired SCA output to the DAC 150 and hence to the SEM screen. When replaying stored data on the SEM screen second gate 146 routes intensity data from the MCA memory 152 to the DAC 150 and hence to the display. The MCS timing circuitry 154 together with the calculation circuitry of the MCA 152 achieves the signal averaging described above.

If the beam sweep is not confined to a single line, but is allowed to raster over the entire image area, the multiple-sweep storage mode can be used to produce a content map. In this case, the user selects a number of "image points" for the entire picture area, which can practically range from 100×100 down to as little as 25×25. All of the information in the square area centered around each point of the image can then be automatically averaged and ultimately can be displayed as a content map. Consider as an example a beam scanning 1000 lines on the sample, and for each line the horizontal sweep subdivided by the integrating time of the ratemeter and channel address in the MCA into 1000 points. If the first twenty sweeps are signal averaged as described above under "stored line scans", and then the contents (which are in counts-per-(live)-second of each group of twenty channels in the scan for each element are averaged, it results in 50 numbers. These are transferred into computer storage, and the process repeated for the next twenty beams scans, and so on.

The result is an array of 50×50 corrected intensity values for each of four elemental energy windows. These data can be "played back" to the SEM display as a brightness-modulated "checkerboard" image for one element at a time, using the ratemeter output circuit as described before. FIG. 7 illustrates the kind of image obtained, as well as the possibility of recording the data using the printer or other hard copy device. Not only can various selections of full scale and log/linear display be used on the stored data, but in addition the content-map image is quite readily interpretable to the eye, in spite of its comparatively poor resolution and small number of image points.

A METHOD FOR PROCESSING STORED LINE SCANS

When multiple element line scans are simultaneously stored, it becomes interesting to use simple modes of data processing to combine them. In many cases we are interested not so much in the variation of one element across the sample as in the relationship between variations of several elements. This is difficult to study with conventional line scans taken one at a time, and even hard to see in the simultaneous scans presented together as were shown in FIG. 7. By adding the capability to store the multiple scans and display any arithmetic combination of them, we introduce the possibility to see the relationships more clearly.

For example, it may be clear that both Ca and Si increase or decrease in the same grains of a material, but by displaying the ratio of Ca/Si (or the inverse) we can see whether the stoichiometry remains essentially the same (neglecting second order effects which would require a full ZAF computation) or not.

A particularly useful extension of this combination or ratioing method results when one of the four energy windows is set on background (typically with several window segments on different portions of the continuum). The background intensity can be used to overcome, to a first order approximation, many of the geometry and density problems described previously.

For example, in a thin section in STEM, the ratio Ca/BG will show real variations in calcium localization independent of the density change associated with the precipitates. Since subtraction can also be easily computed point-by-point on the line scans, it is even better to display the net calcium variation (Ca-BG)/BG for this case.

For bulk samples, the effects of surface geometry can be partially compensated by setting a background window at an energy near the peak of an element of interest, for example FE in a sample containing Fe and S. The effect of changing surface orientation, which particularly changes the absorption path length of the X-rays, is similar for the characteristic X-rays and for the continuum X-rays of nearly the same energy. For example, in a specimen having Fe and S present, the problem can be largely compensated, using the (Fe-BG)/BG signal. The ratio of Fe to S in this specimen can be also shown by the plot of $$\frac{(Fe - BG)/BG}{(S - BG)/BG}$$

where in this case two background windows were set up at energies near the Fe and S peaks. The system allows any arithmetic combination of terms to be selected.

Finally, the same advantages of combining line scans from several elements can also be realized with the stored array of intensities described under content mapping, so that element/element, element/background, and other combinations can be displayed.

Figure 8:
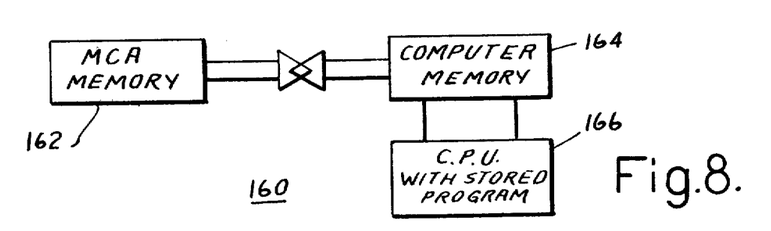
FIG. 8 is a block diagram of a system for manipulation of stored data in a multichannel analyzer memory by external computer hardware.

Manipulation of stored data involves addressing the stored SCA intensities in the MCA memory 162, FIG. 8, and calculating the necessary combinations in external computer hardware 164, 166. When completed, the processed data can be fed back into the MCA 162. The computer used is an LSI-11-3 manufactured by Digital Equipment Corporation.

DISPLAY MEANS FOR MCA & SEM

By storing the SCA data in alternate memory channels of the MCA it is possible using the normal display means of the MCA to display the stored data. This is shown for four SCA intensity channels on FIG. 7.

Although the mode just described can often be viewed and interpreted directly, especially in cases where changes in intensity for one element correspond (positively or inversely) to changes in another, it is still clearly desirable to be able to view and/or photograph the line scan on the SEM display, where it will be in proper registration with the image.

This can readily be accomplished using the existing buffered output circuitry 134 (FIG. 4) of the ratemeter 100, normally used for real-time scans. If as the beam scans across the sample, the counts-per-(live)-second data are taken from one of the stored line scans in memory 152 (FIG. 5) and used to generate the output voltage 88 (FIG. 3) that is passed to the vertical deflection axis of the SEM display, it appears there the same as a real-time scan. This means that multiple-sweep data can be accumulated and the "played out" for viewing, or that data can be taken once and then re-played on the display with different full-scale (or linear/logarithmic) selections.

We claim:

1. A system for improved line scan and X-ray map enhancement of scanning electron microscope data for use with computer controlled collection and processing of energy dispersive X-ray data comprising:
   an energy dispersive X-ray detecting unit;
   a preamplifier/amplifier which amplifies and shapes pulses from said detecting unit;
   a fast discriminator unit which forms a fast discriminator pulse for each pulse coming into said preamplifier/amplifier, such that the fast discriminator pulses may be counted to give an absolute count of the input pulses to said preamplifier/amplifier;
   an analog-to-digital converter to digitize a subset portion of the total number of output pulses of said preamplifier/amplifier, the remaining pulses being rejected;
   a multi-channel analyzer memory unit addressed by said digitized pulses to store the count of said digitized pulses, the address of each digitized pulse being a function of the energy of the incoming X-ray event;
   said multi-channel analyzer memory further including a portion which stores attributes of energy levels for setting energy windows for analyses;
   a single channel analyser pulse shaper which receives pulses from said multi-channel analyzer memory upon receipt of a pulse in the energy window set by the attribute bits of said multi-channel analyzer memory;
   a fast discriminator scaler which serves to count the fast discriminator pulses from said fast discriminator unit;
   a stored pulse scaler which counts each digitized and stored pulse generated by said analog-to-digital converter;
   a single channel analyzer pulse scaler which counts pulses from said single channel analyzer pulse shaper;
   a plurality of scaler buffers to serve as temporary storage for the outputs of said fast discriminator scaler, said stored pulse scaler and said single channel analyzer pulse scaler;
   timing circuitry to control the periodic transfer of data from said scalers to said scaler buffers and to reset said scalers, the timing of said timing circuitry being dependent upon integration times requested by the user of said system;
   means to compute a number equivalent to the dead time corrected intensity level as a count rate; said means being digitally integrating dead time correction circuitry;
   an intensity buffer to receive the calculated corrected intensity;
   means to output the contents of said intensity buffer which is a digital representation of a single channel analyzer intensity;
   a digital-to-analog converter to receive said digital representation of the single analyzer channel intensity and convert said digital representation into an analog representation of intensity count rate in counts-per-live-second;
   means to output said analog representation of intensity count rate for use as a video deflection signal on the Y-axis of the display of a scanning electron microscope thus creating an X-ray line scan.

2. The system of claim 1 further comprising:
   multiple single channel analyzer circuits, the outputs of said multiple single channel analyzer circuits representing multiple single channel outputs from said multiple channel analyzer memory;
   multiple single channel analyzer scalers, the number of said scalers being equal to the number of said single channel analyzer circuits;
   multiplexer circuity for selecting one or more of said single channel analyzer scaler inputs on a sequential basis to feed the contents thereof under the control of said timing circuitry into said digitally integrating dead time correction circuitry;
   switching circuitry to select under the control of said timing circuitry the output of said digital-to-analog converter for each of said single channel analyzer corrected intensities;
   sample and hold circuitry in the form of an analog buffer one such circuit for each of said single channel analyzer inputs to hold said analog signals until required as a voltage for said line scan circuitry.

3. The system of claim 1 wherein the means for correction of dead time whereby the intensity is calculated as counts per live second comprises:
   a digitally integrating dead time correction circuitry having an inputs:
   the count from said fast discriminator scaler which is the total number of stored counts;
   the time over which these counts has been accumulated from said timing circuitry;
   the number of rejected counts determined by subtracting the number of digitized stored pulses from said stored pulse scaler from the number of fast discriminator counts in said fast discriminator scaler;
   arithmetic circuitry to execute the equation; $t^* = t(1-(R/S+R))$, where S is the total number of stored counts, R is the number of rejected counts, $t^*$ is a corrected time, t is the live time and $t^*$ gives resulting intensities in counts-per-live-second for each integration;
   said dead time corrected count forming the basis of an input signal to be held in said intensity buffer.

4. The system of claim 1 further including means to enhance X-ray mapping, said means comprising:
- a voltage threshold connected to the output of said digital-to-analog converter;
- said voltage threshold adjusted by the user and normally corresponding to the count rate associated with background;
- a voltage comparator having an inputs the voltage intensity from said digital-to-analog converter and the voltage threshold;
- a pulse shaper which receives from the voltage comparator all voltages in excess of said voltage threshold;
- an inhibit logic circuit;
- combinatorial logic circuitry which gates said shaped pulses greater than the threshold level to said inhibit logic circuit to inhibit the output of one or more of said single channel analyzers, said threshold serving to gate the dot output such that for a mpa of X-ray dots any dots occurring in a region where the count rate is below the threshold will not be passed to the scanning electron microscope display.

5. The system of claim 4 further including means to set one or more thresholds to inhibit one or more single channel analyzer outputs whereby the output from the single channel analyzer representing one element may be used to discriminate the output of another single channel analyzer representing another element, thereby providing an image which may be interpreted as an X-ray map of compounds instead of elements.

6. The system of claim 4 in which said digital integrating ratemeter functions to enhance patterns of element intensity distribution in X-ray dot maps further comprising:
- multiple single channel analyzer outputs, each of which passes through said inhibit gates to scanning electron microscope circuitry for Z modulation (brightness modulation) of said scanning electron microscope display;
- said inhibit channel signals for each channel being independently generated by said combinatorial logic circuitry;
- said inhibit signal preventing the output of each respective single channel analyzer signal to said scanning electron microscope;
- the Y intensity output of said digital integrating ratemeter being an analog representation of the count rate of at least one of said single channel analyzer pulse trains;
- said V intensity being compared in said voltage comparator with a said user chosen threshold voltage;
- the output of said voltage comparator being shaped in said pulser shaper to be at the correct logical voltage level for said logic circuitry.

7. The system of claim 4 wherein the output of said digital integrating ratemeter is used for the enhancement of X-ray dot maps further comprising:
- means to enable the outputs of a plurality of single channel analyzers to pass through said inhibit gates to the scanning electron microscope circuitry for the brightness modulation of the scanning electron microscope display;
- said inhibit signals for each channel being independently generated by said combinatorial logic circuitry;
- each of said inhibit signals preventing the output of its respective single channel analyzer signal to said scanning electron microscope;
- the threshold intensity being provided by a digital comparison comprising:
  - a digital comparator;
  - a digital representation of a threshold count rate selected by said user serving as one input for said digital comparator;
  - a digital intensity generated by said dead time correction circuitry serving as the other input to said digital comparator;
  - the output signal of said comparator being the signal indicating that the threshold level is greater than the ratemeter intensity level;
- said combinatorial logic circuitry then inhibiting all signal channel analyzer pulses below said threshold level in those single channel analyzer channels selected by the user;
- providing the means to enhance the output of any single channel analyzer by inhibiting its own intensity output resulting in the removal of extraneous background signals from said X-ray dot map, or in the removal of signals from one element in areas deficient in a second element to produce an image which may be interpreted as an X-ray map of compounds instead of elements.

8. The system as claimed in claim 1 further including means to store multiple line scans in said multi-channel analyzer memory, said means comprising:
- circuitry to direct said dead time corrected value of counts-per-live-second directly from said digitally integrating ratemeter to said multi-channel analyzer memory.

9. The system as claimed in claim 8 wherein multiple simultaneously but separately active energy windows in said multi-channel analyzer permit the simultaneous storing of multiple line scans for different elements or energy windows, each one having at least one segment.

10. The system as claimed in claim 9 wherein said means further comprises:
- a combinatorial control logic circuit;
- first gating circuitry which receives under the control of said control logic a digital output from said intensity buffer;
- digital calculation circuitry which receives the digital output of said first gating circuitry and stores the results of its calculation in said MCA memory;
- second gating circuitry operating under the control of said control logic which receives processed or stored inputs from said MCA memory and calculation circuitry;
- said digital-to-analog converter receiving said processed or stored inputs for display on the display of said scanning electron microscope;
- timing circuitry to synchronize the processing storage and retrieval of said intensity data with said scanning electron microscope display.

11. The system of claim 10 further comprising:
- means to process multiple stored lines scans and means to display any arithmetic combination thereof;
- said means providing the displaying of relationships between intensity levels of varying elements and/or compounds, or compensating for typographical, density or thickness variations influencing the intensity levels of one or more elements.

12. The system of claim 9 further including means to improve the statistical quality of stored and displayed lines scans comprising:
- multiple scan sweeps by said scanning electron microscope by a pulse from said single channel analyzer;
- means to store in said multi-channel analyzer memory the data of each line scan;
- calculation circuitry in said multi-channel analyzer to signal average the data from each of said line scans such that with each successive sweep the new value is averaged with prior data with appropriate weighting based on the number of sweeps;
- said calculation circuitry embodying means to execute the following equation for each sweep: where the previously stored count rate value is R0 and the new value is R1, than the subsequently stored value from the Nth sweep will be $$\frac{(N-1)}{n} R_o + \frac{1}{N} R_1 .$$

13. The system of claim 12 wherein said means for storing line scan data comprises:
- first gating circuitry which gates N intensity data from said intensity buffer to said multi-channel analyzer memory;
- said N intensity data from a plurality of single channel analyzers being routed sequentially;
- timing logic to time the routing of said data into said multi-channel analyzer in synchronization with said scanning electron microscope display;
- second gating means permitting the simultaneous displaying of said SCA output data to said digital-to-analog converter and thereafter to said scanning electron microscope display;
- said second gating circuitry routing stored intensity data from said multi-channel analyzer memory to said digital-to-analog converter and thereafter to said scanning electron microscope display;
- said timing circuitry and said calculation circuitry of said multi-channel analyzer serving to signal average the Y modulation of said scanning electron microscope display.

14. The system of claim 1 further including means to display stored line scan data, said means comprising:
- means to store said single channel analyzer data in alternate memory channels of the multi-channel analyzer;
- means to display said stored data by retrieval from said multi-channel analyzer memory in digital form;
- means to position and store said retrieved data in said buffered output circuitry of said digitally integrating ratemeter;
- means to generate the output voltage in said digital-to-analog converter;
- and means to output said voltage to the vertical deflection axis of the scanning electron microscope display.

15. A method of dead time correction for use in energy dispersive X-ray analysis systems to eliminate statistical errors caused by rejected, non-processed pulses comprising:
- presetting an elapsed time T for integration; p1 counting the number of pulses received S during said preset elapsed time;
- counting the number of rejected pulses R during said preset elapsed time;
- measuring the live time t;
- calculating the resulting intensities in counts per live second according to the equation:
- $t^* = t(1-(r/(S+R)))$, thus correcting the live time t such that the corrected live time $t^*$ is determined.

16. A method of X-ray map enhancement and content mapping for use in energy dispersive X-ray analysis systems comprising:
- setting a threshold on the output of a digitally integrating ratemeter corresponding to the count rate of background signals;
- setting a ratemeter integration time;
- gating the output of said ratemeter such that only count rates above the threshold level are passed to a digital to analog converter for display.

17. The method of claim 16 furhter including:
- setting the integration time of a digital integrating ratemeter for a short integration time;
- setting a threshold on the output of a digitally integrating ratementer corresponding to the non-peak count rate associated with at least oné element present in a sample;
- inhibiting the outputs of said digitally integrating ratemeter with respect to said preset thresholds such that only intensities above the threshold levels will be displayed.

18. A method for processing stored line scans for use with an energy dispersive X-ray analysis system comprising:
- storing multiple line scans as intensity levels of single channel analyser outputs in a digital memory device;
- retrieving from memory arithmetic combinations of said stored line scans;
- inhibiting the one single channel analyser output at or near the background intensity;
- displaying the arithmetic combination of a plurality of said stored line scans.

19. The method of claim 18 further comprising:
- inhibiting the output of said digital integrating ratementer for at least one of said outputs of a signal channel analyser to provide a ratio of elements present in a sample.

* * * * *